United States Patent [19]

Diehl

[11] Patent Number: 4,653,131
[45] Date of Patent: Mar. 31, 1987

[54] BED SHEET RESTRAINT

[76] Inventor: Dolores M. Diehl, P.O. Box 1664, Ventura, Calif. 93002

[21] Appl. No.: 759,335

[22] Filed: Jul. 26, 1985

Related U.S. Application Data

[63] Continuation-in-part of Ser. No. 660,706, Oct. 15, 1984, abandoned, which is a continuation-in-part of Ser. No. 529,117, Sep. 2, 1983, abandoned.

[51] Int. Cl.⁴ .......................... A47G 9/02; A61F 13/00
[52] U.S. Cl. ............................................ 5/494; 5/496; 128/134
[58] Field of Search ............................ 5/413, 494–498; 128/133–135

[56] References Cited

U.S. PATENT DOCUMENTS

| | | | |
|---|---|---|---|
| 648,621 | 5/1900 | Hooper | 5/494 |
| 1,241,699 | 10/1917 | Barnes | 5/413 |
| 1,403,873 | 1/1922 | Scott | 5/494 |
| 2,048,097 | 7/1936 | Bjornson | 5/494 |
| 2,677,834 | 5/1954 | Moynihan | 128/134 |
| 2,679,056 | 5/1954 | Simpson | 5/497 |
| 2,702,385 | 2/1955 | Goldberg | 5/413 |
| 2,828,738 | 4/1958 | Strelakos | 128/134 |
| 2,851,703 | 9/1958 | Greco | 5/494 |
| 2,927,581 | 3/1960 | Queen | 128/134 |
| 3,243,827 | 4/1966 | Kintner | 5/496 |
| 3,413,665 | 12/1968 | Amet | 5/496 |
| 3,872,524 | 3/1975 | Hummel | 5/494 |

Primary Examiner—Gary L. Smith
Assistant Examiner—Michael F. Trettel
Attorney, Agent, or Firm—Jack C. Munro

[57] ABSTRACT

A restraint for a bedridden individual which comprises a fabric sheet from which extends a plurality of spaced apart fastening straps from the periphery of the sheet. Each fastening strap is to be secured to a portion of the bed frame with a human being located in the supine position on the mattress being confined within the space formed between the fabric sheet and the mattress. The restraint may include a turtleneck to be located about the neck of the individual.

3 Claims, 9 Drawing Figures

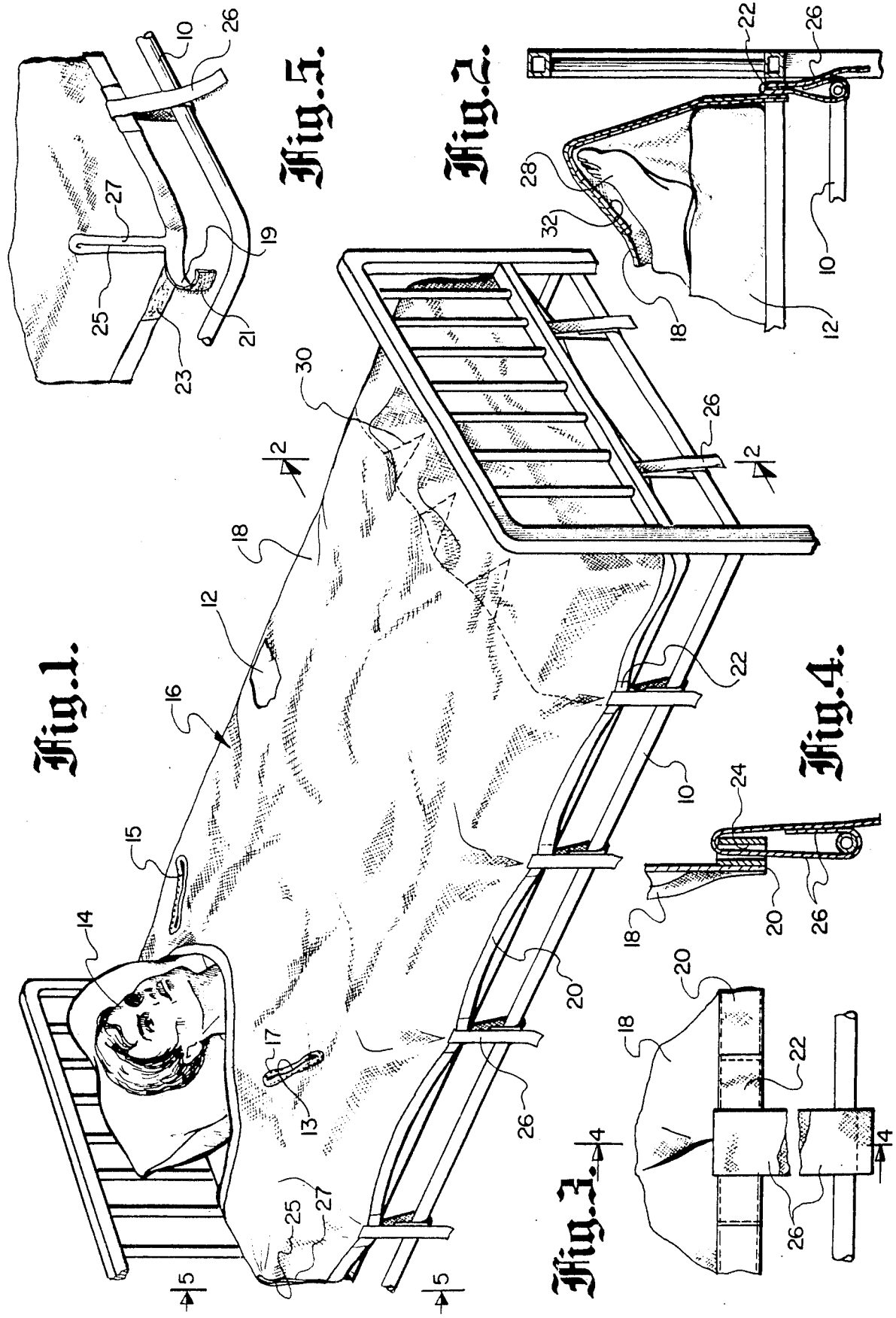

BED SHEET RESTRAINT

REFERENCE TO PRIOR APPLICATIONS

This application is a continuation-in-part of patent application Ser. No. 660,706, filed Oct. 15, 1984 and now abandoned, entitled, "Bed Sheet Restraint" which in turn is a continuation-in-part of patent application Ser. No. 529,117, filed Sept. 2, 1983 and now abandoned, entitled "Bed Restraint".

BACKGROUND OF THE INVENTION

The field of this invention relates to restraints, more particularly to a restraint for a human being which is to be utilized in conjunction with a bed.

Within hospitals and convalescent homes, it is at times necessary to insure that the patient will remain in bed. Certain patients may be senile and if they fall from the bed, the patient can be hurt. Also, other patients may be delirious and it would not be desirable for this type of individual to have freedon of movement. Also with certain types of injuries it may be desirable to restrain the individual to a bed.

Previous attempts of designing bed restraints would normally take the form of a plurality of straps or a vest. The use of the straps is exceedingly confining and gives a patient in essence no mobility extremely limiting the individual's freedom of movement. A vest is somewhat better regarding freedom of movement. However, with the vest, the individual is locked into a single position on the mattress. With geriatrics it only takes a short period of time for bed sores to develop. Holding the individual in a single position causes these bed sores to develop.

It would be desirable to construct some kind of restraint to insure that an individual will remain within a bed, but at the same time gives the individual a greater degree of movement than is possible with other previous types of restraints.

SUMMARY OF THE INVENTION

The restraint of the present invention functions also as a bed sheet which is to be placed over the patient. Located about the peripheral edge of the bed sheet at desired locations are plurality of loops. Each loop is to connect to a strap. The free end of each strap is to be tightly secured onto the bed frame. The sheet is constructed so that the foot of the sheet, where the patient's feet will be located, includes a cavity or pocket. This cavity or pocket can be formed by pleating of the sheet in this particular area. There is a modified version of the restraint which locates the uppermost section of the restraint under the shoulders of the patient. The restraint may also include a resilient yarn collar to be located about the neck of the patient.

BRIEF DESCRIPTION OF THE DRAWINGS

FIG. 1 is an isometric view showing the restraint of the present invention being located over a patient which is confined to a bed;

FIG. 2 is a cross-sectional view through the foot section of the restraint taken along line 2—2 of FIG. 1;

FIG. 3 is an elevational view showing the connection of a strap to a loop;

FIG. 4 is a cross-sectional view taken along line 4—4 of FIG. 3;

FIG. 5 is an enlarged view of a corner of the restraint of this invention taken along line 5—5 of FIG. 1;

DETAILED DESCRIPTION OF THE SHOWN EMBODIMENT

Figure 6:
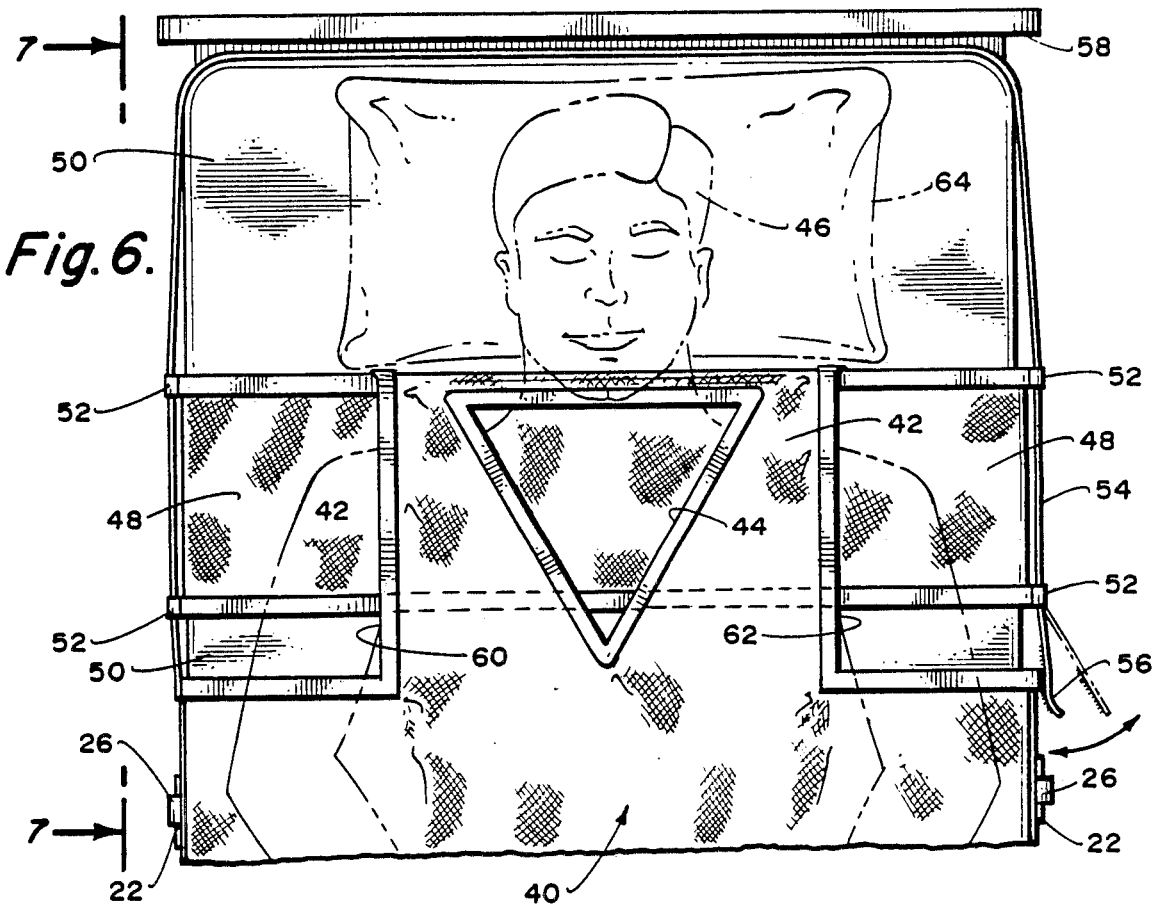
FIG. 6 is a top plan view of the head and shoulder portion of a patient within a bed wherein the patient is restrained by a modified version of a bed sheet restraint of this invention.

Referring particularly to the drawing there is shown in FIG. 1 a conventional bed constructed of a bed frame assembly 10 and a mattress 12. Laying on the mattress 12 is a patient 14. The mattress 12, as well as the bed frame 10, are deemed to be conventional.

The restraint 16 of the present invention is composed principally in the form of a fabric sheet 18 which is to be placed over the patient 14 with the patient located in a supine position. The normal fabric for a sheet 18 would be cotton. Located about the periphery of the sheet 18 is a strip of material 20. Strip 20 has mounted thereon a plurality of short strips 22 which form loops 24. The strips 22 can be attached as by sewing or by other conventional fastening means. It is to be noted that there are a plurality of strips 22. Which are located in a spaced apart relationship about the strip 20. It is to be noted that there are 12 in number of the strips 22. However, it is deemed within the scope of this invention that this number could be increased or decreased as desired.

Connected with each loop 24 is a strap 26. One end of each strap 26 is to pass through a loop 24 to be fastened to itself as is shown in FIG. 4 of the drawing. The fastening to itself is to be removable and variable to different positions. One desirable type would be by using hook and eyelet pads which are marketed under the tradename of "Velcro".

The free end of each strap 26 is to be tied around a portion of the bed frame 10 such as is shown in FIG. 1 of the drawing. It is to be noted that there are 12 in number of the straps 26 with four in number located down each side of the bed and two in number at the foot of the bed and two in number at the head of the bed. At the head of the bed there is a strap located on each side of the patient's head.

In order to accommodate the patient's feet 28, located directly adjacent the foot section of the restraint 16 there is included a series of pleats 30. The pleats 30 function to create a pocket 32. The remaining portion of the sheet 18 is to just lie against the patient 14.

It is to be noted that with the patient 14, located as shown in FIG. 1 of the drawings, the patient is free to move about in the space provided between the sheet 18 and the mattress 12. Actually it has been found that the patient 14 cannot even turn himself over as well as move to various other positions. Therefore, using the restraint 16 of the present invention, the patient is free to move to different positions, thereby eliminating physical problems which do occur when a patient is located in a single position for a long period of time.

It may be desirable to include within the sheet 18 provision for the patient's arms. Therefore, there is included arm openings 13 and 15. Each arm opening 13 and 15 is reinforced by a sewn reinforcing strip 17.

Also, to provide for quick and easy entry and exit of the patient, one fitted corner of the sheet 18 is cut forming edges 25 and 27. To hold these edges together when the restaint 16 is in operation, hook pad 21 is to engage with eyelet pad 23. Hook pad 21 is mounted onto sheet 18 directly adjacent edge 27. Eyelet pad 23 is mounted onto sheet 18 directly adjacent edge 25.

Figure 7:
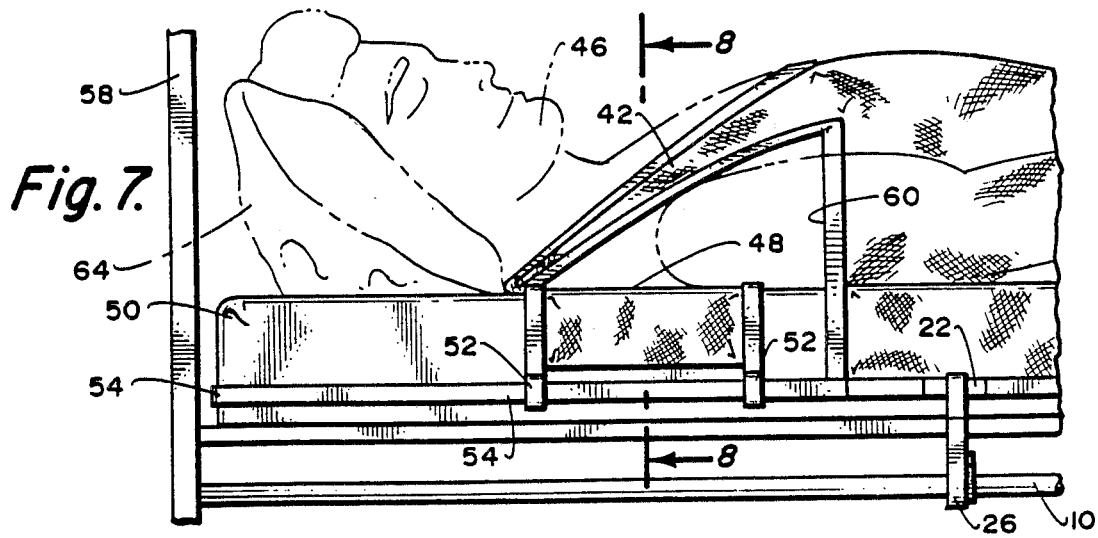
FIG. 7 is a side-elevational view taken along line 7—7 of FIG. 6.
Figure 8:
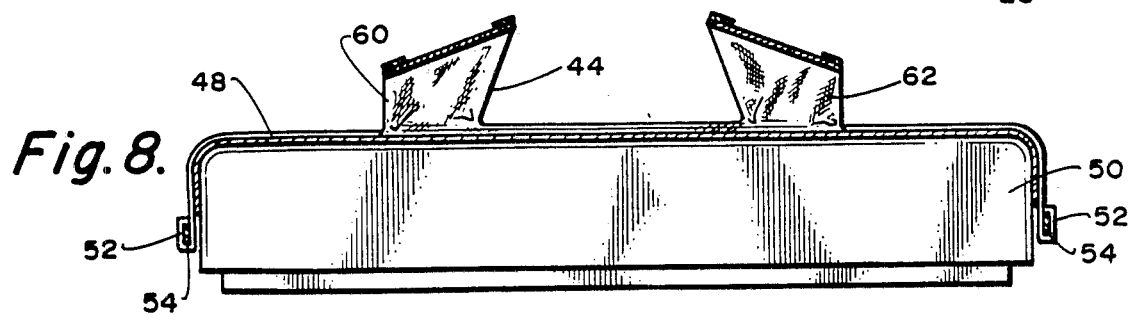
FIG. 8 is a cross-sectional view taken along line 8—8 of FIG. 7.

Referring particularly to FIGS. 6–8 of the drawings, there is shown a modified version 40 of the restraint of this invention. The modified version 40 utilizes a foot section which is basically similar to the foot section of the restraint shown in FIGS. 1-5. The modified version 40 includes a fabric sheet 42 which has laterally centered at the head portion of the sheet 42 a triangular shaped opening 44. The patient's head 46 is to be conducted through the opening 44 with the wall of the opening resting against the neck and shoulder area of the patient.

The uppermost section 48 of the sheet 42 is formed in the shape of a strip which extends the entire width of the sheet 42. This uppermost section 48 is to be turned over to be located between the back of the patient and the mattress 50. Each lateral edge of the uppermost section 48 terminates in a pair of loops 52. A strap 54 is to be conductible through the loops of 52 on one side of the section 48, around the forward end of the mattress 50, and then pass through the loops 52 on the opposite side of the mattress 50. The strap 54 is integrally fixedly secured at one side of the sheet 42 and removably secured through the use of a "Velcro" fastener 56 on the opposite side of the sheet 42. It may be found desirable to have the strap 54 to be conducted around a fixed structure of the bed, such as a portion of the headboard 58, in order to prevent accidental disconnection with the mattress 50.

Located on one side of the sheet 42 directly adjacent the opening 44 is a cutout section 60. A similar cutout section 62 is formed within the sheet 42 on the opposite side of the opening 44. One arm of the patient is to pass through the cutout section 60 with the other arm of the patient passing through cutout section 62.

It is to be understood that with the patient's head 46 being located placed on the pillow 64 and the patient's shoulders pressing against the uppermost section 48, that the patient is securely held in position, thereby totally restraining the patient, yet, at the same time not giving the patient the feeling of being rstrained. Any upward torso movement of the patient is restrained by the patient's own weight pressing against the section 48.

Figure 9:
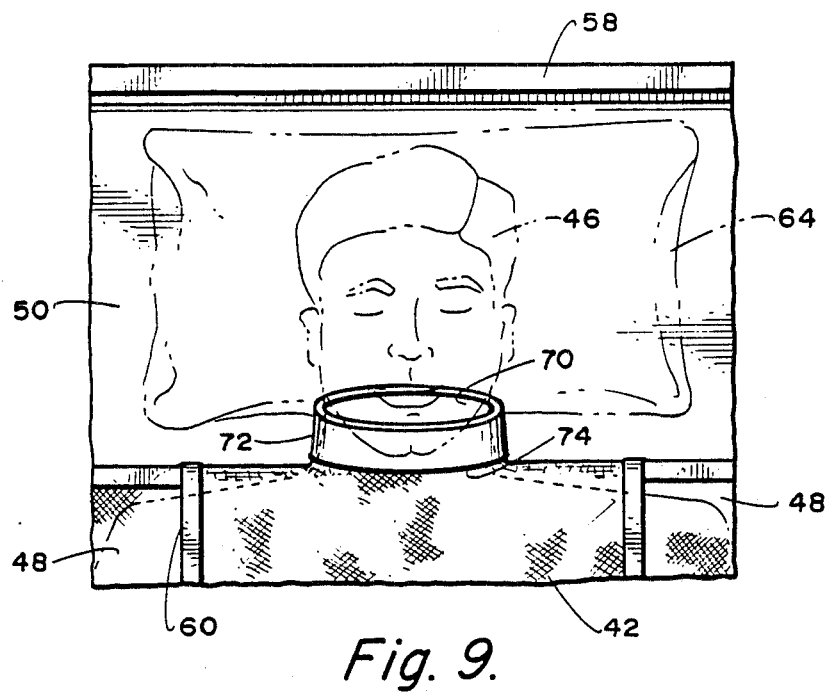
FIG. 9 is a top plan view of the head and shoulder portion of a patient within a bed wherein the patient is restrained by a further modified version of the bed sheet restraint which utilizes a turtleneck.

Referring particularly to FIG. 9, there is shown a further modified version of bed sheet restraint of this invention which utilizes a collar composed of inner section 74 and folded over outer section 72. The collar defines opening 70. The collar is attached to sheet 42. The collar is to be located about the neck of the patient 46. This collar provides for flexible movement of the restraint as the patient moves eliminating any possibility that the patient could choke which may occur with opening 44. The collar is constructed of a resilient (stretchable) material such as loosely knitted yarn to permit expansion but yet closely comforms to the shape of the neck of the patient 46.

What is claimed is:

1. In combination with a bed composed of a bed frame and a mattress, said mattress having a head section adapted to accommodate the head and shoulders of the human being, said matress having a foot section adapted to accommodate the feet of the human being, a restraint to insure that a human being will remain in a supine position on said mattress, said restraint comprising:

a fabric sheet substantially totally covering said mattress, said fabric sheet defining an upper end, said upper end adapted to be folded over onto said fabric sheet to be located between the shoulders of the human being and said mattress, said sheet having a peripheral edge;

a fastening strap assembly composed of a plurality of separate fastening straps, one end of each said fastening strap being attached by a loop to said peripheral edge of said sheet with the other end of each said fastening strap being free, said loop being formed by a cloth strip sewn to the peripheral edge, said other end of each said strap being secured to said bed frame; and an opening formed within said fabric sheet, said opening adapted to be located about the neck of the human being, said opening being located directly adjacent said upper end, an expandable fabric collar attached to said fabric sheet about said opening, said collar to be located in a closely conforming manner about the neck of the human being.

2. The combination as defined in claim 1 wherein:

a securing strap having one end fixedly attached to said fabric sheet and the remaining end removably secured to said fabric sheet, said securing strap to be located about said head section of said mattress, said upper end having a loop member extending therefrom, said loop member to connect with said securing strap.

3. The combination as defined in claim 2 wherein:

said fabric sheet including a pair of arm openings through which the arms of the human being may extend.

* * * * *